(12) United States Patent
Lindemann et al.

(10) Patent No.: US 8,613,761 B2
(45) Date of Patent: Dec. 24, 2013

(54) SURGICAL IMPLANT WITH AN ANTI-BACKOUT FEATURE

(75) Inventors: Gary S. Lindemann, Collierville, TN (US); William David Armstrong, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1083 days.

(21) Appl. No.: 11/863,969

(22) Filed: Sep. 28, 2007

(65) Prior Publication Data
US 2009/0088808 A1 Apr. 2, 2009

(51) Int. Cl.
*A61B 17/70* (2006.01)
*A61B 17/84* (2006.01)
*A61B 17/04* (2006.01)

(52) U.S. Cl.
USPC ........................................................ 606/289

(58) Field of Classification Search
USPC ............. 606/61, 69, 70, 71, 72, 60, 246–299; 623/17.11–17.16
See application file for complete search history.

(56) References Cited

U.S. PATENT DOCUMENTS

| | | | |
|---|---|---|---|
| 5,876,402 A | 3/1999 | Errico et al. | |
| 5,931,838 A | 8/1999 | Vito | |
| 6,258,089 B1 | 7/2001 | Campbell et al. | |
| 6,331,179 B1 | 12/2001 | Freid et al. | |
| 6,398,783 B1 | 6/2002 | Michelson | |
| 6,454,771 B1 | 9/2002 | Michelson | |
| 6,602,255 B1 | 8/2003 | Campbell et al. | |
| 6,626,907 B2 | 9/2003 | Blain et al. | |
| 6,755,833 B1 * | 6/2004 | Paul et al. | 606/70 |
| 7,025,769 B1 * | 4/2006 | Ferree | 606/281 |
| 2002/0004683 A1 * | 1/2002 | Michelson | 623/17.16 |
| 2002/0143336 A1 * | 10/2002 | Hearn | 606/69 |
| 2003/0040749 A1 | 2/2003 | Grabowski et al. | |
| 2004/0030338 A1 * | 2/2004 | Paul | 606/69 |
| 2004/0034352 A1 | 2/2004 | Needham et al. | |
| 2005/0021032 A1 * | 1/2005 | Koo | 606/69 |
| 2005/0234455 A1 | 10/2005 | Binder et al. | |
| 2005/0283152 A1 | 12/2005 | Lindemann et al. | |
| 2006/0149233 A1 | 7/2006 | Richelsoph | |
| 2006/0161157 A1 * | 7/2006 | Mosca et al. | 606/69 |
| 2006/0217725 A1 * | 9/2006 | Suh | 606/71 |
| 2006/0229620 A1 * | 10/2006 | Rothman et al. | 606/69 |
| 2006/0293669 A1 | 12/2006 | Lindemann et al. | |
| 2007/0118125 A1 | 5/2007 | Orbay et al. | |
| 2007/0123884 A1 * | 5/2007 | Abdou | 606/69 |
| 2009/0264934 A1 * | 10/2009 | Youssef et al. | 606/280 |

FOREIGN PATENT DOCUMENTS

WO 2006098906 A1 9/2006

OTHER PUBLICATIONS

International Searching Authority, International Search Report, Dec. 11, 2008.
International Searching Authority, Written Opinion, Dec. 11, 2008.

* cited by examiner

*Primary Examiner* — Kevin T Truong
*Assistant Examiner* — Christopher Beccia

(57) ABSTRACT

The present application is directed to an implant maintained within the patient by a fastener. The implant includes an aperture sized to receive the fastener. A locking member extends across the aperture in a first position. The locking member is constructed of a resilient material that is movable to a second position during insertion of the fastener. Once the fastener is inserted within the aperture below a level of the locking member, the locking member rebounds towards the first position and extends over the fastener. The locking member prevents the fastener from backing out of the implant.

13 Claims, 6 Drawing Sheets

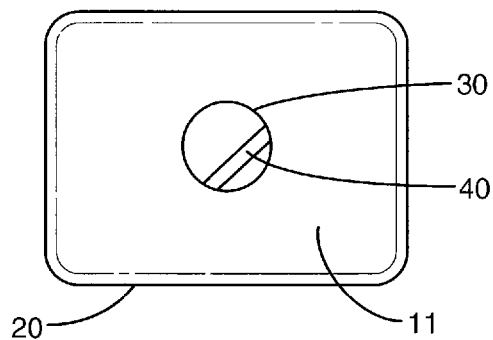
FIG. 13
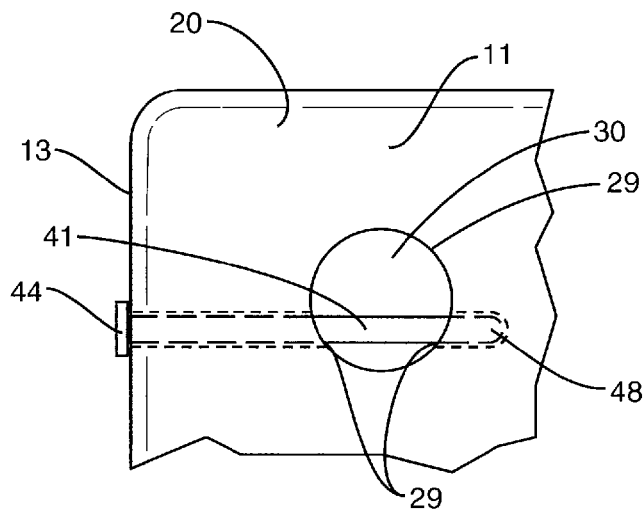
FIG. 14
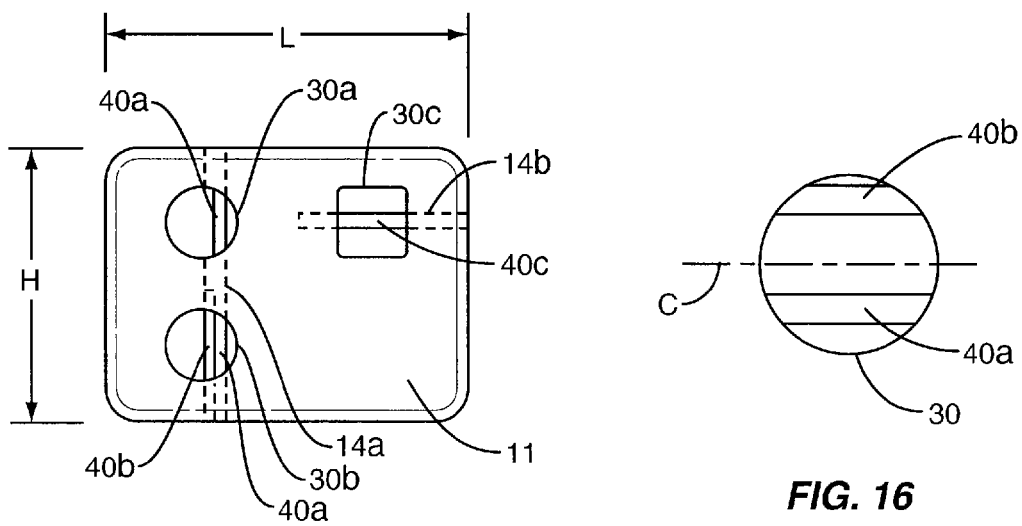
FIG. 15
FIG. 16

SURGICAL IMPLANT WITH AN ANTI-BACKOUT FEATURE

BACKGROUND

The present application is directed to implants maintained within a patient with one or more fasteners and, more particularly, to an implant with a locking member to prevent backout of the fasteners.

Various types of implants may be mounted within a patient. One example includes a plate sized to extend along an exterior of a femur to treat a fracture. Another example is a plate that extends along one or more vertebral members to support and/or strengthen the vertebral members. Another type of implant is a spacer that is inserted into an intervertebral space formed between two vertebral members.

The implants include one or more apertures each sized to receive a fastener to mount the implant at the appropriate position within the patient. Various types of fasteners may be used, such as screws, pins, rivets, and the like. The fasteners are inserted through the apertures and driven into bone.

A problem with some fasteners is the tendency to backout of the bone after the initial mounting. Backout may be caused by movement of the patient after the fasteners are inserted, changes in the underlying bone in which the fasteners are mounted, or miscellaneous other reasons. Backout is problematic as a head of the fastener extends outward above a surface of the implant. The head may cause injury to the surrounding tissue and/or discomfort to the patient. Backout is further problematic because the implant may move from the appropriate position within the patient. This movement may prevent the implant from performing the expected function for which it was originally implanted into the patient. Further, the movement may cause injury to the bone, surrounding bone or tissue, and/or discomfort to the patient.

SUMMARY

The present application is directed to a surgical implant with an anti-backout feature. The implant may include a body with an aperture. The aperture may be bounded by a sidewall. The sidewall may include first and second spaced-apart and distinct guide holes. A resilient locking member may be positioned within the body and extend across the aperture and through the first and second spaced-apart guide holes. In one embodiment, the locking member divides the aperture, when viewed generally normal to the front face, into first and second open areas each bounded by the locking member and the sidewall.

BRIEF DESCRIPTION OF THE DRAWINGS

FIG. 13 is a front schematic view of an aperture within the body according to one embodiment.

FIG. 14 is a partial front schematic view of an implant according to one embodiment.

FIG. 15 is a partial front schematic view of a section of an implant according to one embodiment.

FIG. 16 is a front schematic view of an aperture and locking members according to one embodiment.

DETAILED DESCRIPTION

The present application is directed to an implant maintained within the patient by a fastener. The implant includes an aperture sized to receive the fastener. A locking member extends across the aperture. The locking member is constructed of a resilient material that is movable to allow insertion of the fastener. Once the fastener is inserted below a level of the locking member, the locking member rebounds over the fastener. The locking member prevents the fastener from backing out of the implant.

Figure 1:
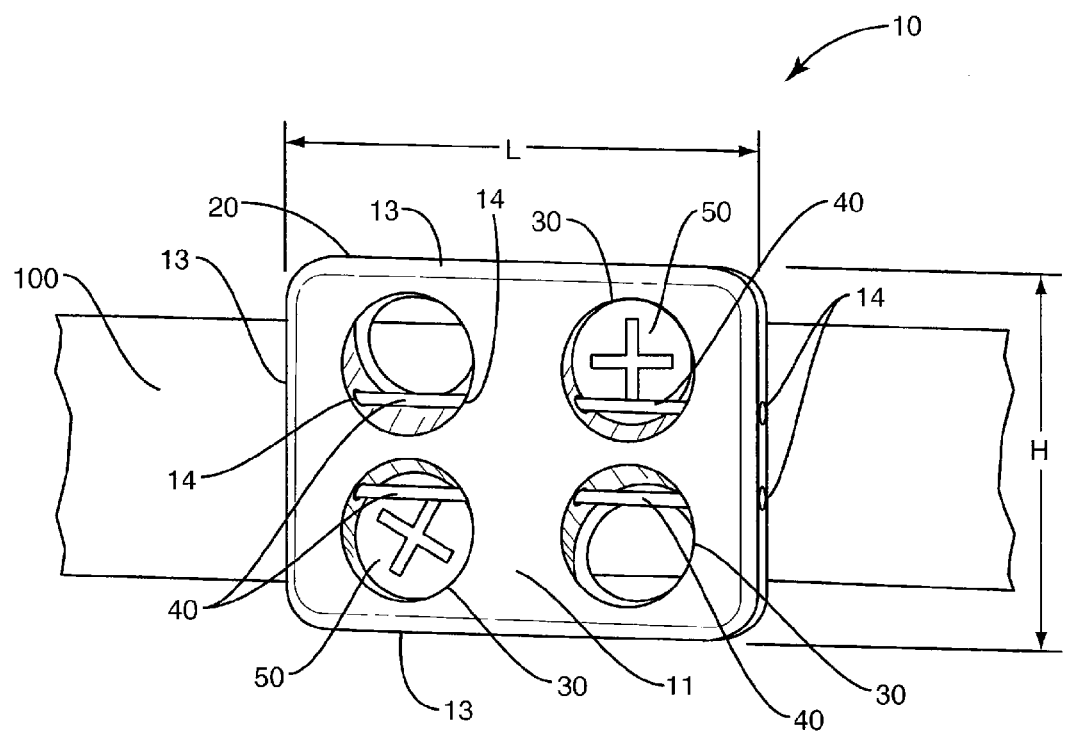
FIG. 1 is a perspective view of an implant according to one embodiment.

FIG. 1 illustrates one embodiment of an implant 10 positioned on a bone 100. The implant 10 includes a body 20 with apertures 30. In this embodiment, the body 20 includes four apertures 30 with fasteners 50 positioned in two of the apertures 30. A locking member 40 extends across each of the apertures 30. Each of the locking members 40 may be part of a single locking member 40. Alternatively, two or more separate locking members 40 may be used to extend across the multiple apertures 30. The locking members 40 are movable from a first position as illustrated in FIG. 1, to a second position that allows insertion of the fasteners 50 into the apertures 30. After insertion of the fastener 50, the corresponding locking member 40 returns towards the first position and extends over the fastener 50 to prevent inadvertent backout.

Figure 2:
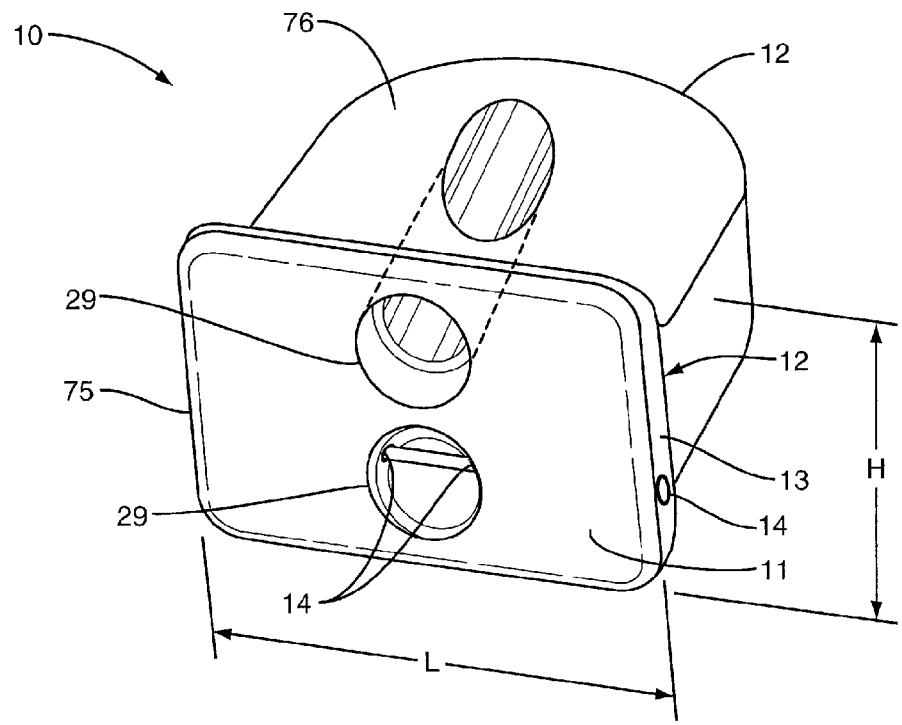
FIG. 2 is a perspective view of an implant according to one embodiment.

Implant 10 may be shaped and sized to perform a variety of different functions. FIG. 1 includes the implant 10 as a plate that extends across an exterior of one or more bones 100. FIG. 2 includes the implant 10 as an intervertebral spacer sized to fit between vertebral members. It is understood that various other types of implants 10 may also be used with the locking members 40 of this application. Likewise, the implant 10 may be positioned at a variety of locations within the patient. Examples of positions for the implant 10 within the patient include but are not limited to against the femur, humerus, tibia, fibula, and one or more vertebral members.

The implant 10 includes a body 20 that may have a variety of sizes and shapes. The body 20 includes a first side 11 and an opposite second side 12. The first side 11 may face outward from the bone 100 and may be visible to the surgeon. The second side 12 is opposite from the first side 11. One or both of the sides 11, 12 may be formed by different sections of the body 20. By way of example in FIG. 2, the second side 12 is formed in part by a back side of a plate 75 that abuts against an exterior surface of vertebral members, and in part by an end of an intervertebral section 76 that is positioned within the intervertebral space. An exterior perimeter wall 13 is formed by one or more exterior lateral sides that extend between the first and second sides 11, 12. The exterior perimeter wall 13 may be perpendicular to one or both of the first and second sides 11, 12.

One or more apertures 30 are positioned within the body 20 and extend from the first side 11 to the second side 12. Each of the apertures 20 is sized to receive a fastener 50 and is bounded by a sidewall 29. The sidewalls 29 may be positioned at a variety of angles relative to the front side 11. The number of apertures 30 may vary depending upon the context of use, including but not limited to four apertures 30 as illustrated in the embodiment of FIG. 1, two apertures 30 in the embodiment of FIG. 2, and a single aperture 30 as illustrated in FIG. 13. In embodiment with multiple apertures 30, the apertures 30 may include the same or different sizes and shapes.

Apertures 30 may be located at various positions within the body 20. FIG. 13 includes a single aperture 30 positioned at a center of the front side 11. FIG. 2 includes a pair of apertures 30 on the front side 11 at a common position along the length L and at different positions along the height H. FIG. 15 includes three apertures 30a, 30b, 30c. Apertures 30a and 30b are located at a common length, and apertures 30a and 30c at a common height H.

Figure 3:
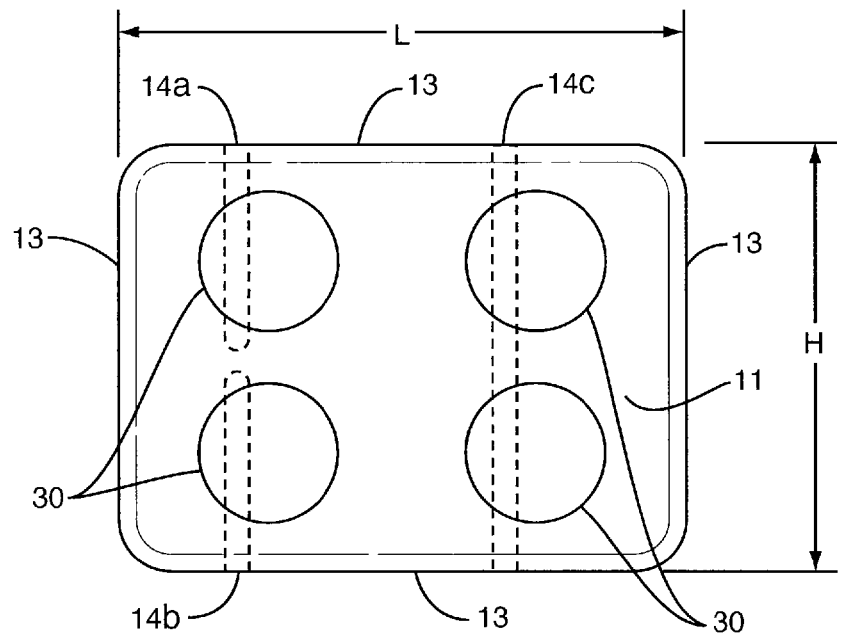
FIG. 3 is a front schematic view of a body of an implant according to one embodiment.

One or more guide holes 14 extend into the body 20 from the exterior perimeter wall 13 and are sized to receive a locking member 40. In one embodiment, the guide holes 14 extend inward from the exterior perimeter wall 13 to at least one of the apertures 30. By way of example, FIG. 3 includes an embodiment with first and second guide holes 14a, 14b each extending inward from the exterior perimeter wall 13 through one aperture 30. Each of these guide holes 14a, 14b extends into the body 20 a limited distance on an opposite side of the respective apertures 30. A third aperture 14c extends the height H of the body 20 and through two apertures 30 two opposing sides of the exterior perimeter wall 13.

Guide holes 14 extend on each side of the apertures 30 to support the locking member 40. This positioning provides for the locking member 40 to be supported on each side of the apertures 30.

Figure 17:
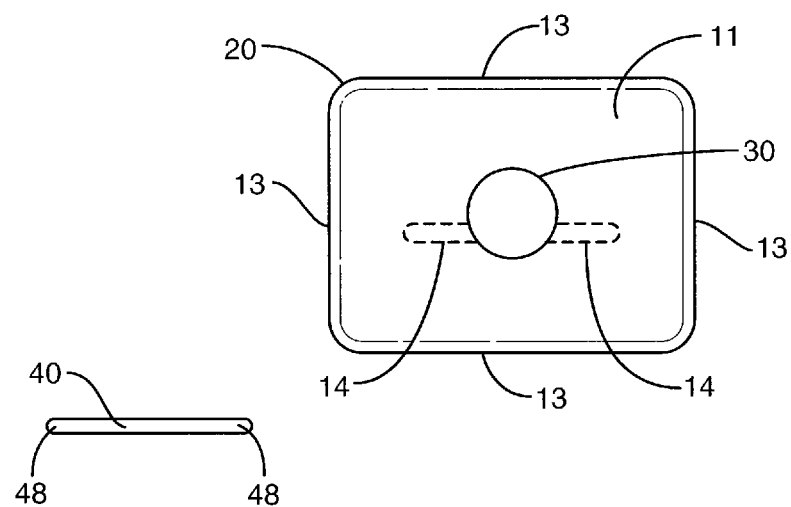
FIG. 17 is an exploded schematic view of an implant according to one embodiment.

FIG. 17 includes an embodiment with guide holes 14 positioned within an interior of the body 20 such that they do not extend to the exterior perimeter wall 13. The guide holes 14 are positioned on opposing sections of the aperture 30 and are sized to receive one or more locking members 40.

Figure 4:
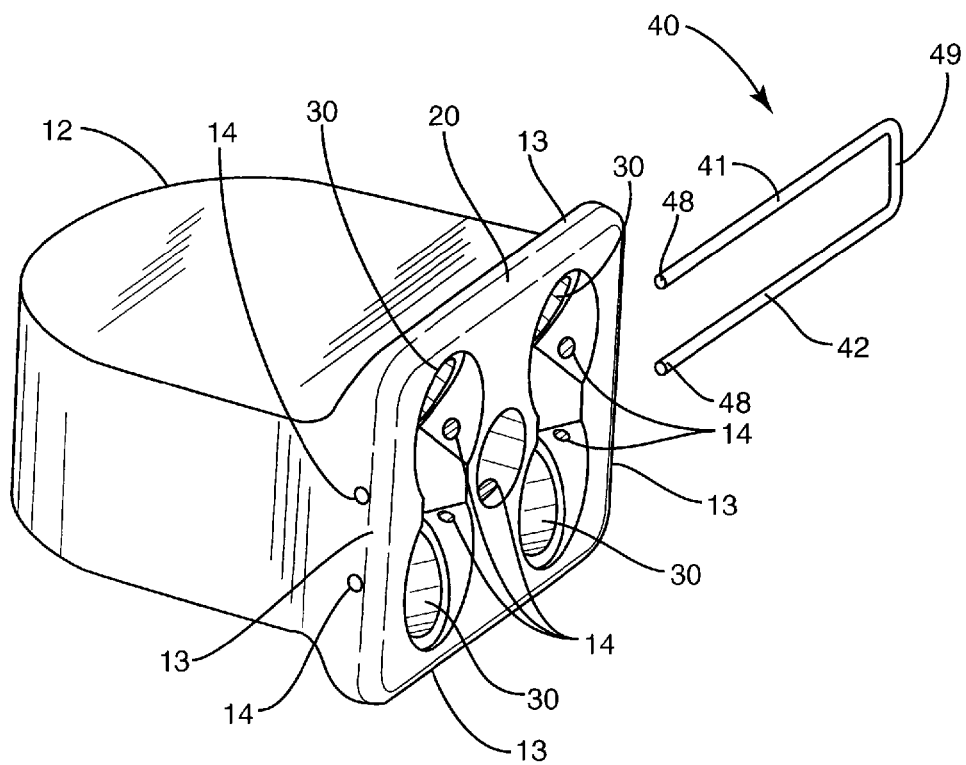
FIG. 4 is an exploded perspective view of an implant according to one embodiment.

Locking member 40 extends across the apertures 30 to prevent backout of the fasteners 50. FIG. 4 illustrates an embodiment of a locking member 40 sized to fit within the guide holes 14. Locking member 40 includes first and second legs 41, 42 with an intermediate connector 49. The legs 41, 42 are substantially straight and include a length to extend at least through the two apertures 30 along the length of the guide holes 14. In one embodiment, the length of the legs 41, 42 is substantially equal to the length L of the body 20 such that the ends of the legs 41, 42 are flush with the exterior lateral side 13 when the locking member 40 is fully inserted into the body 20. Legs 41, 42 may also be shorter than the length L such that the ends terminate within an interior of the body 20.

Figure 6:
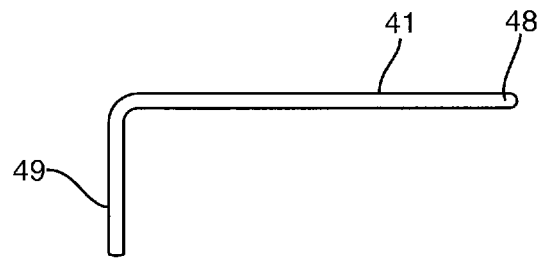
FIG. 6 is a schematic view of a locking member according to one embodiment.

Locking member 40 may also include various other shapes and sizes. FIG. 6 includes an embodiment with a single leg 41.

Figure 9:
FIG. 9 is a section view of an arm of a locking member according to one embodiment.
Figure 7:
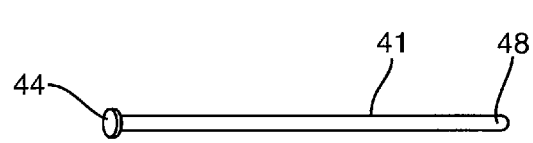
FIG. 7 is a schematic view of a locking member according to one embodiment.
Figure 10:
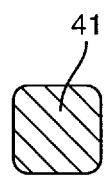
FIG. 10 is a section view of an arm of a locking member according to one embodiment.
Figure 8:
FIG. 8 is a schematic view of a locking member according to one embodiment.
Figure 11:
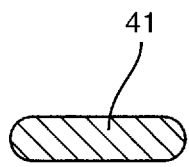
FIG. 11 is a section view of an arm of a locking member according to one embodiment.

FIG. 7 includes a single leg 41 with an enlarged head 44 at one end. Head 44 includes a greater width than the leg 41 and a greater width than the guide holes 14 and remains on the exterior of the body 20 during insertion of the locking member 40. FIG. 8 includes a single leg 41 with no head. The locking member 40 may include a variety of cross-sectional shapes. FIG. 9 includes an embodiment with the leg 41 with a circular sectional shape, FIG. 10 includes a rectangular sectional shape, and FIG. 11 includes an elongated oval sectional shape. In one embodiment with multiple legs 41, 42, each of the legs 41, 42 includes a different sectional shape.

Figure 12A:
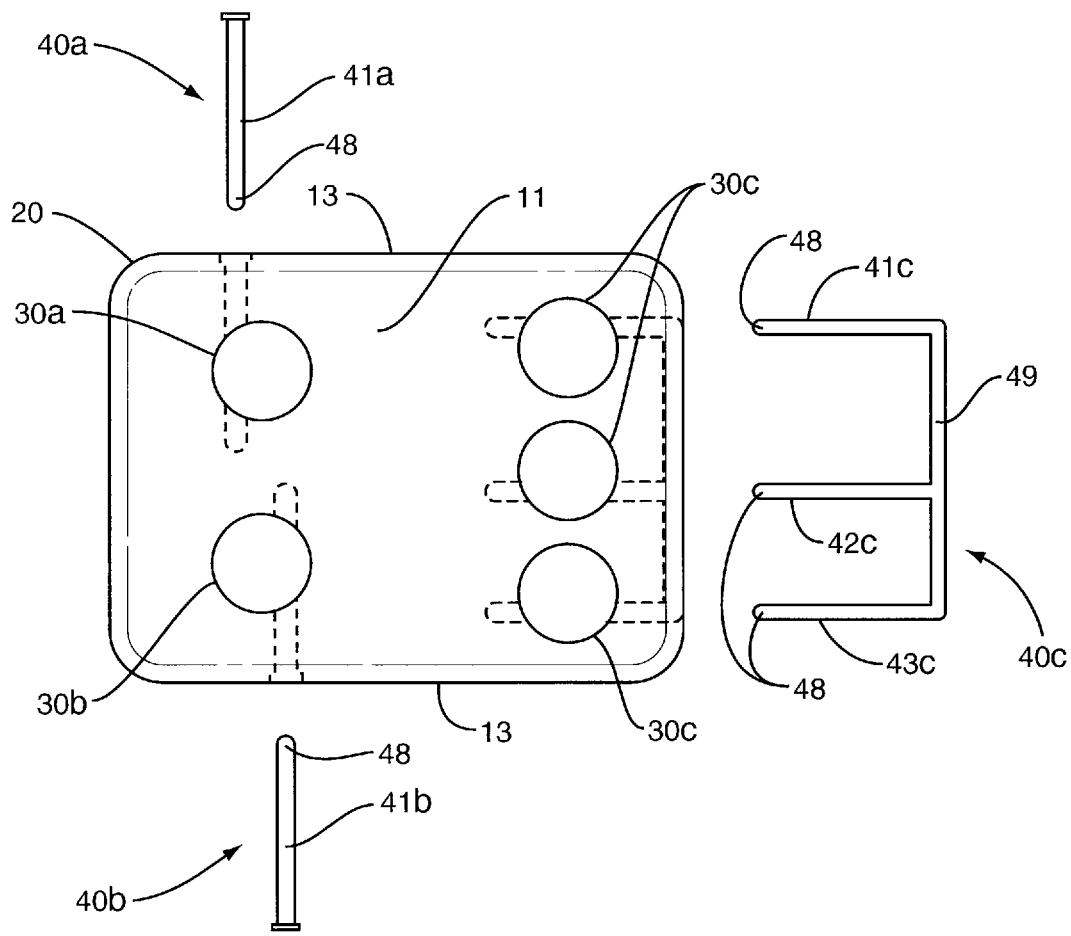
FIG. 12A is an exploded front schematic view of an implant according to one embodiment.
Figure 12B:
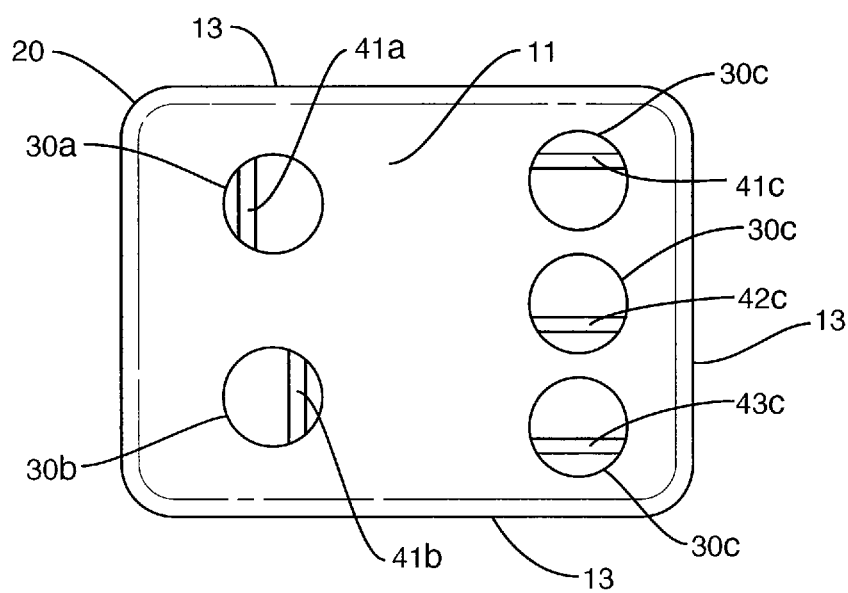
FIG. 12B is a schematic front view of the constructed implant illustrated in FIG. 12A.

FIGS. 12A and 12B include an embodiment with multiple locking members 40. A first locking member 40a is sized to extend into the exterior perimeter wall 13 from a first direction and across a first aperture 30a. A second locking member 40b extends inward from an opposite side of the exterior perimeter wall 13 and across a second aperture 30b. A third locking member 40c extends inward from an adjacent side of the exterior perimeter wall 13 and includes three legs 41c, 42c, and 43c connected together by a connector 49. Each of the legs 41c, 42c, 43c extends across one of the apertures 30c.

The locking member 40 is constructed of a resilient material having elastic properties. The locking member 40 is deformable to move away from the aperture 30 during insertion of the fastener 50. In one embodiment, the locking member includes a curved shape to move away from the aperture 30. After the fastener 50 passes beyond the locking member 40, the locking member 40 returns towards its original shape and position within the aperture 30. The locking member 40 may completely or partially return to the original shape and position. In one embodiment, the locking member 40 is made of a Nickel-Titanium alloy that is heat treated to achieve superelastic properties when exposed to a temperature range within the human body. The locking member 40 may also be constructed of other materials including but not limited to PEEK, titanium, and stainless steel.

FIG. 14 illustrates one embodiment of the arm 41 of the locking member 40 extending across the aperture 30. The aperture 30 includes two guide holes 14 that are spaced apart along the sidewall 29. Each of the guide holes 14 is discrete and independent. The locking member 40 is inserted into the guide hole 14 within the exterior perimeter wall 13. In this embodiment, locking member includes a single arm 41 with a head 44 at one end. During insertion, the arm 41 is inserted into the guide hole 14 and moved through the body 20. Arm 41 is moved through the aperture 30 and into the guide hole 14 on the opposite side of the aperture 30. When the locking member 30 is fully inserted into the body 20, the head 44 contacts against the exterior perimeter wall 13.

FIG. 15 includes an embodiment with multiple locking members 40a, 40b extending across one of the apertures 30b. The locking members 40a, 40b are each positioned within guide hole 14a. Locking member 40a includes an extending length to also extend across aperture 30a.

FIG. 17 includes an embodiment with the locking member 40 sized to fit within the guide holes 14. Locking member 40 is deformed from its original straight shape during insertion into the aperture 30. Once aligned, the locking member 40 is released to extend within the guide hole 14 and across the aperture 30.

The locking members 40 may be positioned away from a centerline C of the apertures 30. As illustrated in FIG. 16, the locking members 40a, 40b are positioned away from the centerline C. This positioning facilitates the locking members 40a, 40b to move away from the centerline C of the aperture 30 during insertion of the fastener 50.

Figure 5:
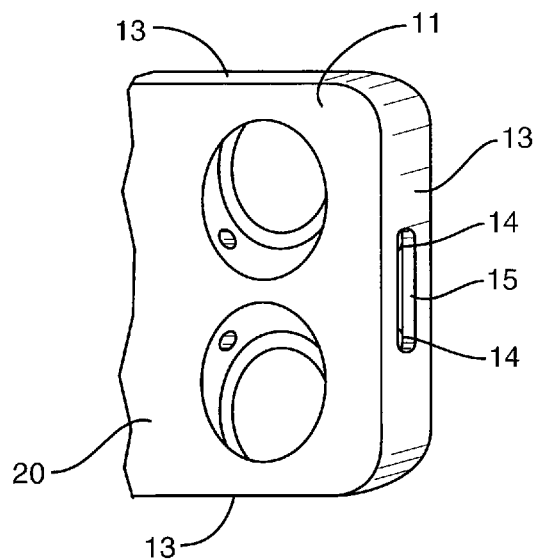
FIG. 5 is a partial perspective view of a groove in an exterior perimeter wall of the body according to one embodiment.

In one embodiment as illustrated in FIG. 5, body 20 may include a groove 15 within the exterior perimeter wall 13. Groove 15 is sized to receive the connector 49 of the locking member 40 (see FIGS. 4 and 6) when the locking member 40 is fully inserted within the body 20. Groove 15 may include a depth such that the connector 49 is flush or recessed within the exterior perimeter wall 13.

The locking member 40 may be attached to the body 20 in a variety of different manners. In one embodiment, the locking member 40 is press fit into the guide hole 14. The size of the guide hole 14 may be slightly smaller than the locking member 40. This sizing allows for the locking member 40 to be forced into the guide hole 14 and form a secure attachment. In one embodiment as illustrated in FIG. 17, the positioning of the guide holes 14 provide attachment. Once the locking member 40 is placed within the guide holes 14, the length of the locking member 40 prevent inadvertent removal and forms a secure attachment. In one embodiment, groove 15 on the exterior perimeter wall 13 includes an undercut section. When the locking member 40 is fully inserted into the body 20, the connector 49 is positioned within the undercut to form a secure attachment. Locking member 40 may also be attached to the body by a fastener or adhesive.

A procedure for using the implant 10 initially includes the surgeon positioning the implant 10 within the patient. Once positioned, a fastener 50 is inserted into the aperture 30. During insertion, the locking member 40 moves from the first position to a second position away from a center of the aperture 30 to allow for insertion of the fastener 50. In one embodiment, the locking member 40 includes a curved shape in the second position. The locking member 40 remains in the second position as the fastener 50 is inserted into the bone 100. After a head of the fastener 50 passes beyond the locking member 40, the resilient locking member 50 rebounds towards the first position and across the aperture 30. The locking member 50 extends over the head of the fastener 50 thus preventing the fastener 50 from backing out of the bone 100 and away from the body 20. In one embodiment, the section of the locking member 40 that extends across the aperture 20 is substantially straight prior to fastener insertion and after the fastener moves beyond the locking member 40.

The locking member 40 may extend across the aperture 30 and is support at two positions along the sidewall 29. The two support positions may be formed by guide holes 14 within the aperture 30, such as the embodiment illustrated in FIG. 14. In another embodiment, the locking member 40 extends into the aperture 30 through a guide hole 14 with an end 48 of the locking member abutting against a section of the sidewall 29 that is spaced away from the guide hole 14. This allows the locking member 40 to include two support positions with the first being the guide hole 14, and the second where the end 48 contacts the sidewall 29.

Figure 18:
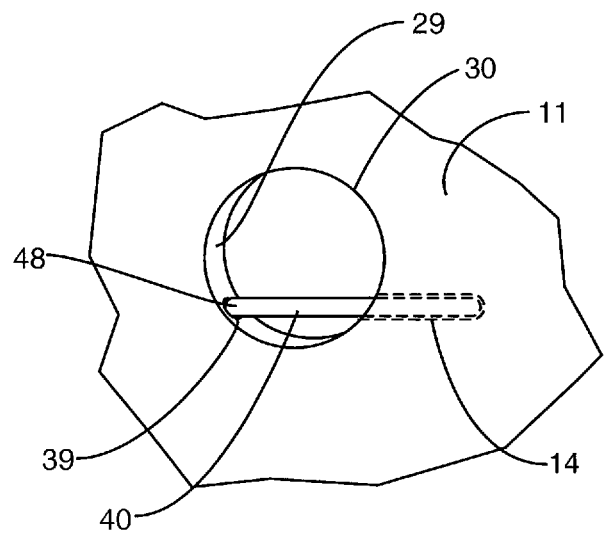
FIG. 18 is a partial front perspective view of a locking member extending within an aperture according to one embodiment.

FIG. 18 includes another embodiment with an indent 39 formed in the sidewall 29. Indent 39 extends into sidewall 29 a limited distance just enough to capture the end 48 of the locking member 40. The end 48 of the locking member 40 contacts against and is supported by the bottom of the indent 39. The depth of the indent 39 is adequate to prevent the end 48 from moving out of the indent 39 during deformation of the locking member 40 that occurs during insertion of the fastener 50.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A surgical implant with an anti-backout feature, the implant comprising:
   a body having a front face, a back face, and an exterior perimeter sidewall extending therebetween, the exterior perimeter sidewall including an exterior surface;
   a first aperture extending through the body from the front face to the back face and being bounded by a first sidewall;
   a second aperture extending through the body from the front face to the back face and being bounded by a second sidewall, the second aperture being spaced away from the first aperture; and
   a resilient locking member having a first leg, a second leg, and a connector, the first and second legs being transverse to the connector;
   wherein the first and second legs extend into the body with the first leg extending across the first aperture, the second leg extending across the second aperture, and the connector extending along a section of the exterior perimeter sidewall and in contact with the exterior surface.

2. The implant of claim 1, further comprising a guide hole extending from the exterior perimeter sidewall of the body to aperture, the locking member positioned within the guide hole.

3. The implant of claim 1, further comprising an indent formed in the sidewall with the connector of the locking member positioned within the indent.

4. The implant of claim 1, wherein the locking member includes a section that extends across the aperture, the section being movable from a first straight shape to a second non-straight shape.

5. The implant of claim 1, wherein the locking member is positioned within the body between the front face and the back face.

6. A surgical implant with an anti-backout feature, the implant comprising:
   a body with a front face, a back face, and an exterior perimeter sidewall extending therebetween;
   a groove extending into the exterior perimeter sidewall;
   an aperture extending through the body from the front face to the back face; and
   a guide hole extending into the body between the front and back faces and into the aperture, the guide hole extending through the exterior sidewall at the groove;
   a resilient locking member with an elongated leg and a connector, the leg being transverse to the connector, the leg including a smaller cross-sectional size than the guide hole to fit within the guide hole;

the resilient locking member is movable from a first position where the leg extends into the exterior surface and is away from the aperture and a second position where the leg extends into the aperture, the connector being spaced away from the groove in the first position and seated in the groove in the second position.

7. The implant of claim 6, wherein the leg and the connector are both substantially straight.

8. The implant of claim 6, further comprising a second aperture extending through the body from the front face to the back face, the locking member extending through the aperture and the second aperture.

9. A surgical implant with an anti-backout feature, the implant comprising:
- a body with a front face and a back face and an exterior perimeter wall extending therebetween;
- first and second apertures each extending through the body, the first aperture being positioned through the body at different height than the second aperture;
- a locking member including an intermediate connector section disposed between and connecting outwardly-extending first and second legs; the first and second legs positioned within the body with:
  - the first leg extending across the first aperture;
  - the second leg extending across the second aperture;
  - the intermediate connector section positioned against the exterior perimeter wall;
- wherein the first and second legs extend through their respective apertures substantially parallel to each other in a first direction;
- wherein the first and second apertures are spaced apart from each other in a second direction perpendicular to the first direction.

10. The implant of claim 9, wherein the first leg extends across the first aperture and divides the first aperture, when viewed generally normal to the front face, into first and second open areas each bounded by the first leg and a sidewall of the first aperture.

11. The implant of claim 9, wherein each of the first and second apertures includes spaced-apart guide holes, with the guide holes of the first aperture sized to receive the first leg and the guide holes of the second aperture sized to receive the second leg.

12. The implant of claim 9, further comprising a third aperture extending through the body from the front face to the back face and being positioned at a same height as the first aperture, the first leg of the locking member extending through each of the first aperture and the third aperture.

13. The implant of claim 9, wherein the exterior perimeter wall includes a groove; wherein the intermediate connector section is disposed in the groove.

* * * * *